(12) United States Patent
Peters

(10) Patent No.: US 7,303,576 B2
(45) Date of Patent: Dec. 4, 2007

(54) VEIN STABILIZER

(76) Inventor: Paul Peters, 400 Diplomat Pkwy. Apt. 214, Hallandale, FL (US) 33009

( * ) Notice: Subject to any disclaimer, the term of this patent is extended or adjusted under 35 U.S.C. 154(b) by 436 days.

(21) Appl. No.: 11/011,608

(22) Filed: Dec. 15, 2004

(65) Prior Publication Data

US 2006/0129184 A1   Jun. 15, 2006

(51) Int. Cl.
*A61B 17/00* (2006.01)
*A61B 17/12* (2006.01)
*A61B 17/132* (2006.01)

(52) U.S. Cl. ............ 606/201; 606/203; 606/204; 24/169; 24/190

(58) Field of Classification Search ........ 606/201, 606/203, 204; 604/116, 179; 128/95.1; D24/169, 190
See application file for complete search history.

(56) References Cited

U.S. PATENT DOCUMENTS 1,824,516 A * 9/1931 Tyvand ............. 606/203
2,185,571 A    1/1940 Robinson
3,167,072 A    1/1965 Stone et al.
3,760,803 A    9/1973 Boothby
4,196,735 A    4/1980 Ayer
4,314,568 A * 2/1982 Loving ............. 606/201
5,312,350 A    5/1994 Jacobs
5,668,784 A * 9/1997 Iguchi ............. 368/282
6,551,285 B1* 4/2003 Bierman ............. 604/180

* cited by examiner

Primary Examiner—Michael J. Hayes
Assistant Examiner—Katherine Dowe
(74) Attorney, Agent, or Firm—Jacobson Holman PLLC

(57) ABSTRACT

The vein stabilizer is a small device that: 1) isolates the vein, so it cannot roll from side to side when penetrated; and 2) causes the vein to bulge toward the surface of the skin making it more apparent. The vein stabilizer includes a sterile, two-piece disposable plastic device that isolates the vein in between two plastic tabs which are similar in shape and size. One tab is fixed on the skin on one side close to the vein. The other piece is mobile and slides on an elastic band. The tabs are adjusted to the preference of the IV initiator or the situation on the other side of the vein (big vein, small vein, tortuous vein, collapsed vein, sclerous (hardened) vein, obese patient, etc.).

7 Claims, 3 Drawing Sheets

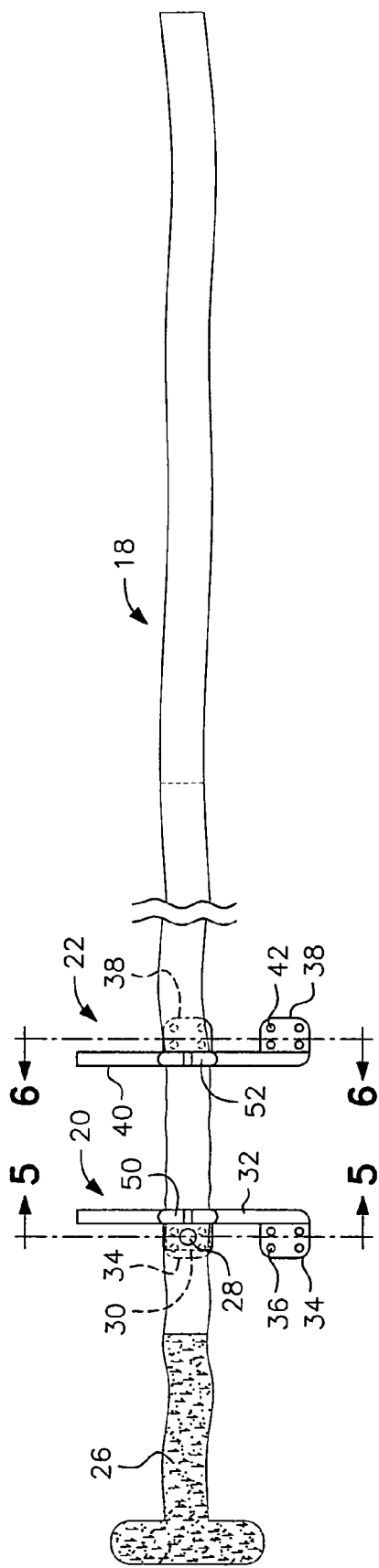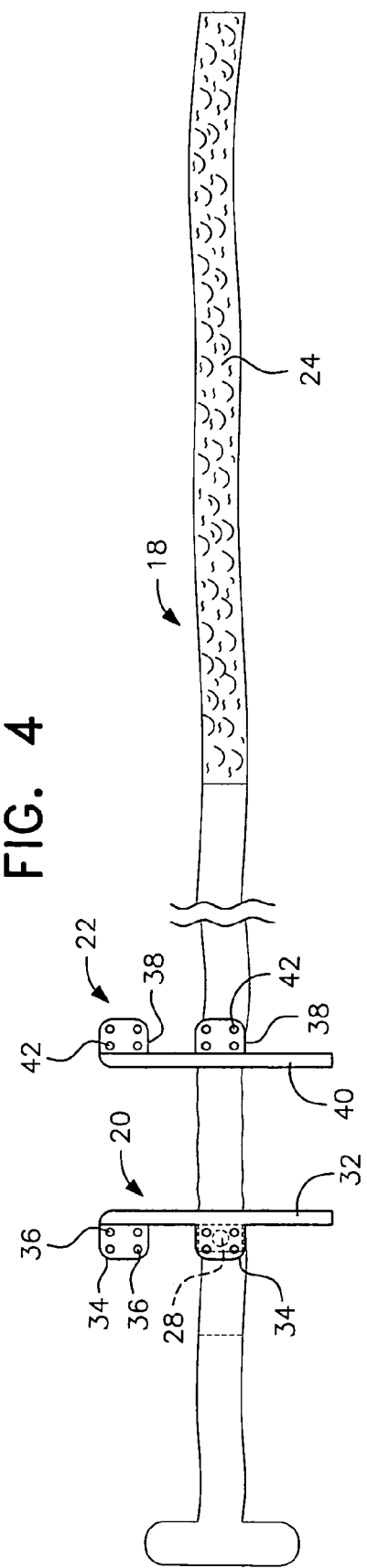

VEIN STABILIZER

FIELD OF THE INVENTION

The present invention includes a vein stabilizer that: 1) isolates the vein, so it cannot roll from side to side when penetrated; and 2) causes the vein to bulge toward the surface of the skin making it more apparent.

BACKGROUND OF THE INVENTION

Veins are often difficult to find and stabilize in order to inject a needle, to draw blood, or establish an intravenous (IV) line. The process can be time consuming, frustrating for nurses, and painful for patients. The veins in the hands and the inferior part of the forearms are not naturally stabilized by connective tissue, so they easily roll when affected by needle sticks. Hematomas can result making the vein unusable temporarily, or permanently thrombosed (clogged).

The difficulties caused by a delay in starting "stat" IV lines can cause discomfort for patients. These discomforts can occur for anyone and at anytime, but mainly occur in elderly, obese patients, poor circulatory status patients, overused veins, agitated patients and children, for example.

Accordingly, there is a long felt need to establish a prominent vein for introduction of an IV needle in a minimum amount of time, regardless of the status or condition of a patient.

SUMMARY OF THE INVENTION

The vein stabilizer of the present invention is a small device that: 1) isolates the vein, so it cannot roll from side to side when penetrated; and 2) causes the vein to bulge toward the surface of the skin making it more apparent.

The vein stabilizer of the present invention includes a sterile, two-piece disposable plastic device that isolates the vein in between two plastic tabs which are similar in shape and size. One tab is fixed on the skin on one side close to the vein. The other piece is mobile and slides on an elastic band. The tabs are adjusted to the preference of the IV initiator or the situation on the other side of the vein (big vein, small vein, tortuous vein, collapsed vein, sclerous (hardened) vein, obese patient, etc.). The slot formed between these two tabs where the vein is isolated, is adjustable to various widths to accommodate varying vein sizes of male/female patients, adults, elderly and children. The device accommodates different anatomical directions of the veins.

The device allows a hands-free procedure once attached due to the elastic strap (tourniquet-like) that surrounds the hand or forearm and is provided with a hook and loop fastener, such as a VELCRO attachment system, at both extremities of the encircling elastic board for tightening in a circle around the hand or forearm. This procedure can be done in seconds. The isolation and stabilization of the vein is to be done in two simple steps.

The first step includes surrounding the area where a desired vein is located with an elastic strap. Mounted on the elastic strap are two tabs. One of the tabs is fixed in position and the other tab is slidable along the strap. Initially, the fixed tab is positioned on one side of the vein.

In the second step, the second tab is moved adjacent to the vein on the other side of the vein from the fixed tab. The proximity of the two tabs on opposite sides of a vein, causes a compression of the skin immediately proximate to the vein. This causes the vein to bulge or become prominent through the skin. The vein held between the two tabs does not have room to move or roll when the force of a penetrating needle is applied. Therefore, the vein is not only made prominent but stabilized in position for an accurate needle penetration.

A hook and loop fastener is used to secure the position of the strap. One of the tabs is secured by a rivet to the strap while the other tab includes a slot through which the strap may pass for sliding movement of the tab on the strap. Both of the tabs include two plates which extend perpendicular to a main body of the tab. Each of the plates includes a plurality of, preferably four, openings which when laid in contact with the skin serve to anchor the tab on the skin and prevent sliding of the tab. In addition, each of the tabs include a projection for anchoring one end of the tab in position on the skin.

Accordingly, it is an object of the present invention to provide a vein stabilizer having two tabs mounted on a strap.

It is yet another object of the present invention to provide a vein stabilizer having two tabs mounted on a strap with one of the tabs being anchored on the strap and the other tab being slidable on the strap.

It is still yet another object of the present invention to provide a vein stabilizer having two tabs mounted on a strap with one of the tabs being anchored on the strap and the other tab being slidable on the strap with each of the tabs including two plates and a projection for anchoring the tabs on the skin.

It is still yet another object of the present invention to provide a vein stabilizer having two tabs mounted on a strap with one of the tabs being anchored on the strap and the other tab being slidable on the strap with each of the tabs including two plates and a projection for anchoring the tabs on the skin with the strap being adjustably secured around the hand or forearm for adjustable placement of the strap.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 3 is a plan view of the elongated strap and two tabs mounted on the strap.

FIG. 4 is a bottom view of the strap and tabs mounted on the strap.

DETAILED DESCRIPTION OF THE PREFERRED EMBODIMENTS

Figure 1:
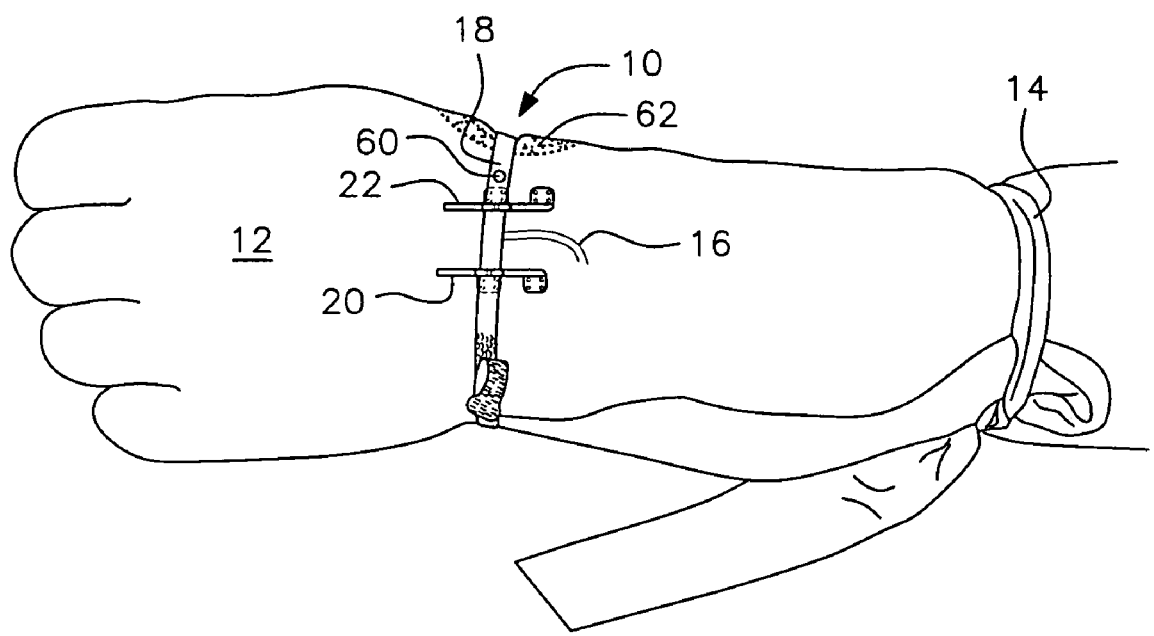
FIG. 1 schematically illustrates an initial placement of the vein stabilizer of the present invention on the hand of a patient.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Figure 2:
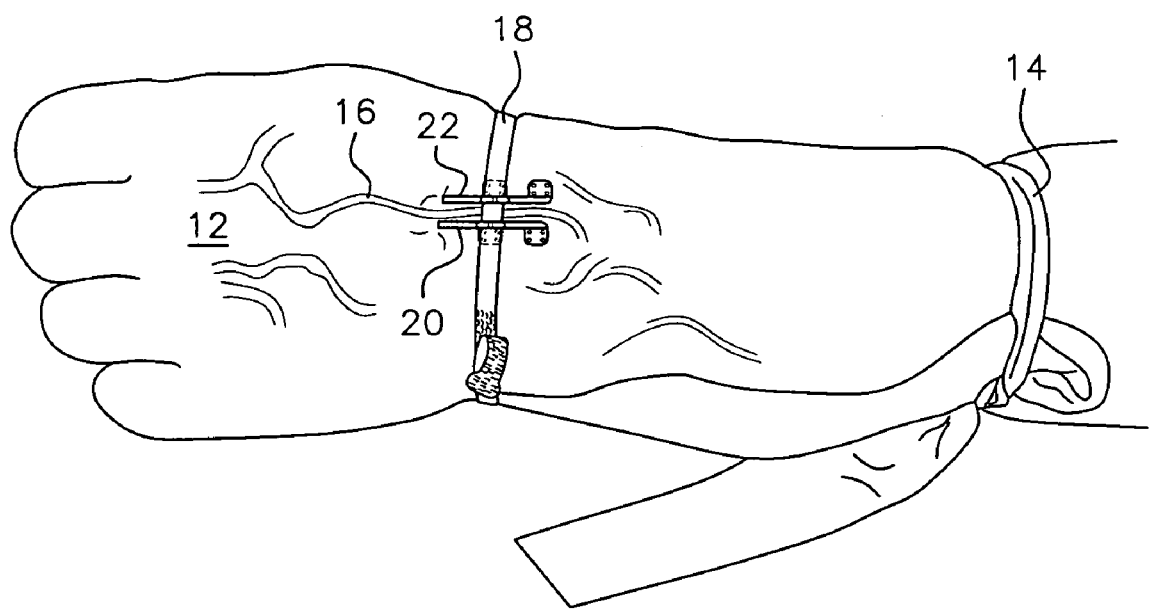
FIG. 2 schematically illustrates the movement of the tabs adjacent to a vein so as to help expose the vein and stabilize the vein during penetration by a needle.
Figure 5:
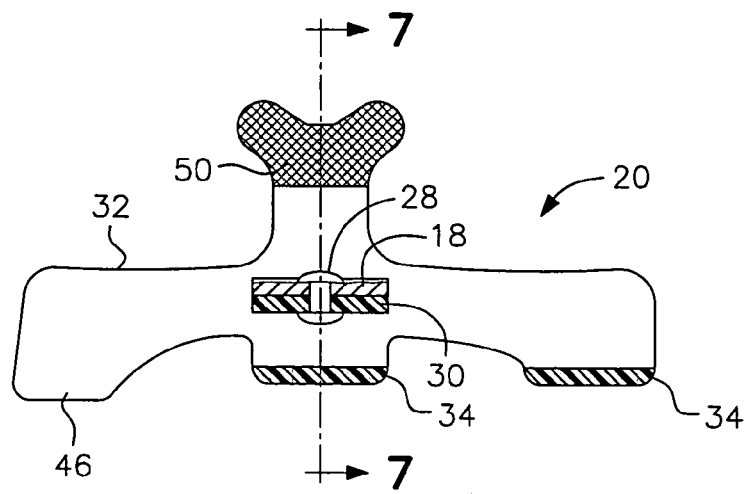
FIG. 5 is a sectional view taken along line 5-5 of FIG. 3 to illustrate a tab fixed to the strap.

With reference to the drawings, in general, and to FIGS. 1 and 2, in particular, the vein stabilizer embodying the teachings of the subject invention is designated as 10. With reference to its orientation in FIG. 1, the vein stabilizer is shown mounted on the hand 12 of a patient. A tourniquet 14 has been placed on the forearm to help in locating a vein 16 which needs to be pierced to initiate transfer of an intravenous solution or other medication.

The vein stabilizer includes an elongated strap 18 and two tabs 20, 22. Tab 20 is fixed on the strap 18, whereas tab 22 is slidably mounted on the strap 18. Tab 22 is slidable on the strap to move, at its furthest limit, into engagement with plastic stop 60. Stop 60 prevents tab 22 from migrating beyond a sterile field into non-sterile area 62.

As shown in FIG. 2, by placement of the tab 20 adjacent to the vein 16 and movement of the tab 22 proximate to the tab 20, a pinch area is formed between the two tabs. Projecting from this pinch area between the two tabs, the vein 16 appears prominently and easily accessible. Due to the proximity of the two tabs, typically with a separation distance of ¾ of an inch and preferably ½ inch, the vein is prominently displayed therebetween. During insertion of a needle into the vein, the vein is fixed in position thereby helping ensure penetration during a first attempt without rollover or movement of the vein.

The specific components of the vein stabilizer 10 are illustrated with reference to FIGS. 3 through 8. In FIGS. 3 and 4, the elongated strap 18 having a width of 0.5 cm is shown having a loop portion 24 of a hook and loop fastener. On a opposite side of the strap 18 is a hook portion 26 of the hook and loop fastener. By wrapping the elongated strap 18 around the hand or arm of a patient, the hook portion 26 engages the loop portion 24 as shown in FIGS. 1 and 2 to secure the strap 18 in place.

Figure 7:
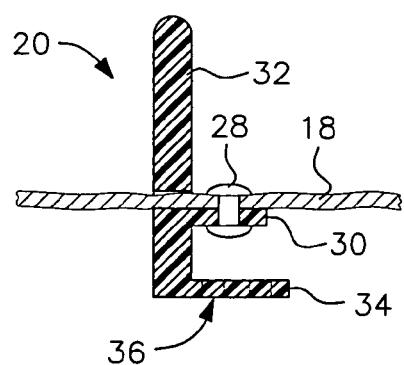
FIG. 7 is a sectional view taken along line 7-7 of FIG. 5.

As shown in FIG. 3, the tab is secured to a strap by a rivet 28 which extends through a plate 30 of the tab 20. The plate 30 extends perpendicular to a main portion 32 of the tab 20 as shown in FIG. 7. The main portion 32 has a thickness of 0.1 cm and a width of 2 cm.

The tab 20 also includes two additional plates 34 which also extend perpendicular to the flat vertically extending main portion 32 of the tab 20 as shown in FIGS. 3 and 4. The plates 34 each include four holes or openings 36 extending through the thickness of the plates 34. These holes 36, when contacting the skin as shown schematically in FIGS. 1 and 2, serve to force portions of the skin into the holes 36 so as to stabilize the tabs on the skin. It is thereby difficult to move the tabs relative to the skin when the skin is engaged by the holes 36 of the plates 34.

Tab 22 similarly, includes two plates 38 which extend perpendicular to a main flat vertically extending portion 40 of the tab 22. A plurality of four holes or openings 42 are located in each of the plates 38.

Figure 6:
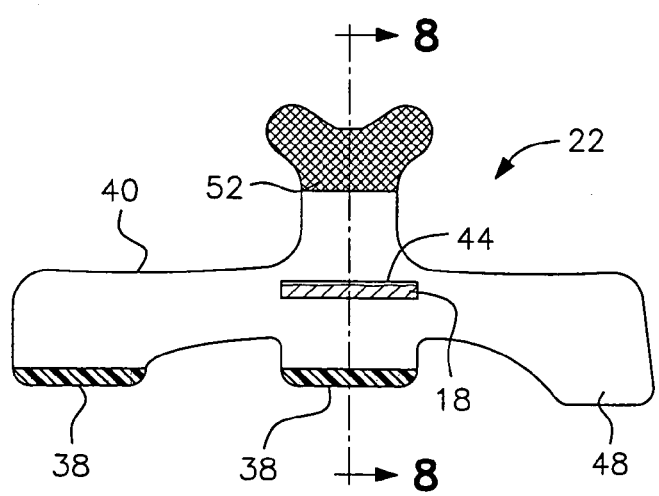
FIG. 6 is a sectional view taken along line 6-6 of FIG. 3 to illustrate a tab slidably mounted on the strap.
Figure 8:
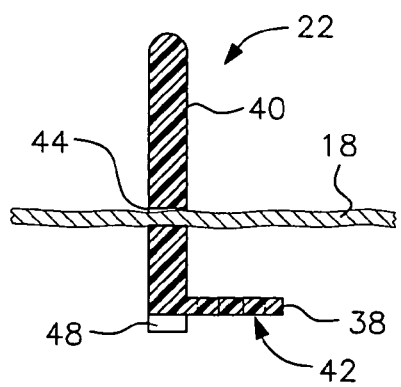
FIG. 8 is a sectional view taken along line 8-8 of FIG. 6.

In addition, in main portion 40 of the tab 22, a slot 44 is formed for passage therethrough of elongated strap 18 as shown in FIGS. 6 and 8. The tab 22 is thereby able to be moved proximate to tab 20 and therefore define a distance between which is located a vein of the patient.

In addition, each of the tabs 20, 22 include a projection portion 46, 48, respectively, which extends below the level of the plates 34, 38, of the tabs 20, 22, respectively. While the plates 34, 38 are engaging and forcing the skin of the patient into the holes in these plates, the projecting portions 46, 48 also serve to stabilize the tabs 20, 22 on the surface of the skin of the patient by engaging the skin and preventing twisting of the tabs. The secure placement of the tabs 20, 22, prevents a shifting or rolling of the vein when contacted with a needle for initiation of an IV line, for example.

The two tabs 20, 22 also include a handle portion 50, 52, projecting from a remainder of the tabs for 0.7 cm, respectively for engagement and locating of the tabs on the skin of the patient. The handle portions are knurled for a secure gripping and movement of the tabs 20, 22.

Accordingly, by the vein stabilizer of the present invention, a vein is captured in an adjustable space between two tabs mounted on an elongated strap. The movement of one of the tabs towards the other pinches a vein in the space between the tabs causing a prominent display of the vein for initiation of an IV line. The vein is stabilized between the two tabs for a secure piercing of the vein by a needle.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A vein stabilizer to be mounted on a hand or a forearm of a patient, said vein stabilizer comprising:
   an elongated strap having two ends interconnected to completely encircle the hand or the forearm of the patient, and
   two separate tabs mounted on the elongated strap, one of the two separate tabs being fixed to the elongated strap and the other of the two separate tabs being slidably mounted on the elongated strap towards and away from the one tab for pinching a vein of the patient between the two tabs and causing protrusion of the vein from the skin for piercing by a needle,
   a portion of said elongated strap extending a shortest distance between said two separate tabs to help maintain a relative positioning of said two separate tabs with respect to each other,
   each of the two separate tabs includes an L-shape having a vertically extending main portion and two separate plates extending perpendicular to the main portion,
   the elongated strap passing through the vertically extending main portion of the other of said two separate tabs,
   the vertically extending main portion of the two separate tabs, respectively, being located opposed to each other on opposite sides of the portion of said elongated strap extending the shortest distance between said two separate tabs.

2. The vein stabilizer as claimed in claim 1, wherein each of the plates includes a plurality of holes.

3. The vein stabilizer as claimed in claim 2, wherein there are four holes.

4. The vein stabilizer as claimed in claim 1, wherein one of the two separate plates extends from a central portion of the main portion and the other of the two plates extends from one end of the main portion.

5. The vein stabilizer as claimed in claim 4, wherein an opposite end of the main portion from the plate at the one end of the main portion, helps engage the patient and stabilize the two separate tabs on the patient.

6. The vein stabilizer as claimed in claim 1, wherein the elongated strap includes a hook portion of a hook and loop fastener on one side of the elongated strap and a loop portion of the hook and loop fastener on an opposite side of the elongated strap.

7. The vein stabilizer as claimed in claim 1, wherein the one of the two separate tabs fixed to the strap is fixed to the strap by a rivet.

* * * * *